(12) United States Patent
Karubian

(10) Patent No.: US 7,585,303 B2
(45) Date of Patent: Sep. 8, 2009

(54) ENHANCED PRODUCTS AND PROCESSES FOR REMOVING CAVITY TISSUE

(76) Inventor: Laurence Karubian, 11715 Folkstone La., Bel Air, CA (US) 90077

( * ) Notice: Subject to any disclaimer, the term of this patent is extended or adjusted under 35 U.S.C. 154(b) by 768 days.

(21) Appl. No.: 11/171,849

(22) Filed: Jun. 30, 2005

(65) Prior Publication Data

US 2007/0000510 A1 Jan. 4, 2007

(51) Int. Cl.
*A61B 17/50* (2006.01)
(52) U.S. Cl. .................................................. 606/134
(58) Field of Classification Search ............... 606/134, 606/133, 162, 131; 132/206; 401/1, 2, 5; D28/44; 222/1, 146.2, 470, 485, 501; 221/135
See application file for complete search history.

(56) References Cited

U.S. PATENT DOCUMENTS

| | | | | |
|---|---|---|---|---|
| 4,282,877 A * | 8/1981 | Mathews | ............... | 606/134 |
| 4,923,448 A * | 5/1990 | Ennis, III | ............... | 604/239 |
| 4,958,951 A * | 9/1990 | Mann | ............... | 401/1 |
| 5,141,348 A * | 8/1992 | 'tartt | ............... | 401/179 |
| 5,188,256 A * | 2/1993 | Nottingham et al. | ............... | 222/1 |
| 5,544,787 A * | 8/1996 | Malofsky | ............... | 222/105 |
| 5,713,914 A * | 2/1998 | Lee | ............... | 606/162 |
| 5,843,043 A * | 12/1998 | Markus | ............... | 604/239 |
| 5,873,666 A * | 2/1999 | Bourke et al. | ............... | 401/1 |
| 5,980,536 A * | 11/1999 | Jamali | ............... | 606/134 |
| 6,027,513 A * | 2/2000 | Massana Florensa | ............... | 606/134 |
| 6,174,319 B1 * | 1/2001 | Desnos | ............... | 606/133 |
| 6,273,625 B1 * | 8/2001 | Martinez de San Vincente Oliveras | ............... | 401/1 |
| 6,478,493 B1 * | 11/2002 | Cepeda et al. | ............... | 401/49 |
| 6,926,457 B2 * | 8/2005 | Vidal Esmoris | ............... | 401/1 |
| 2003/0187463 A1 * | 10/2003 | Cooper | ............... | 606/134 |
| 2004/0037608 A1 * | 2/2004 | Cochran | ............... | 401/1 |

* cited by examiner

*Primary Examiner*—Anhtuan T Nguyen
*Assistant Examiner*—Sarah A Simpson
(74) *Attorney, Agent, or Firm*—Peter J. Gluck; Technology Law Group; Luce Forward Hamilton & Scripps LLP.

(57) ABSTRACT

Improved devices for removing tissue, for example nasal hair using natural wax. One embodiment uses telescoping tubes and there is wax or glue located in the inner tubes or between the tubes, whereby the tubes are located so that the inner one can extend or retract relative to the outer tube. Following heating the wax or glue for softening purposes, the same is applied to the inner part of the nasal cavity by emplacing the same in a desired naris and through application of force and wax extrusion through a cloth boot or otherwise, in combination with mild external pressure, removal is accomplished.

8 Claims, 5 Drawing Sheets

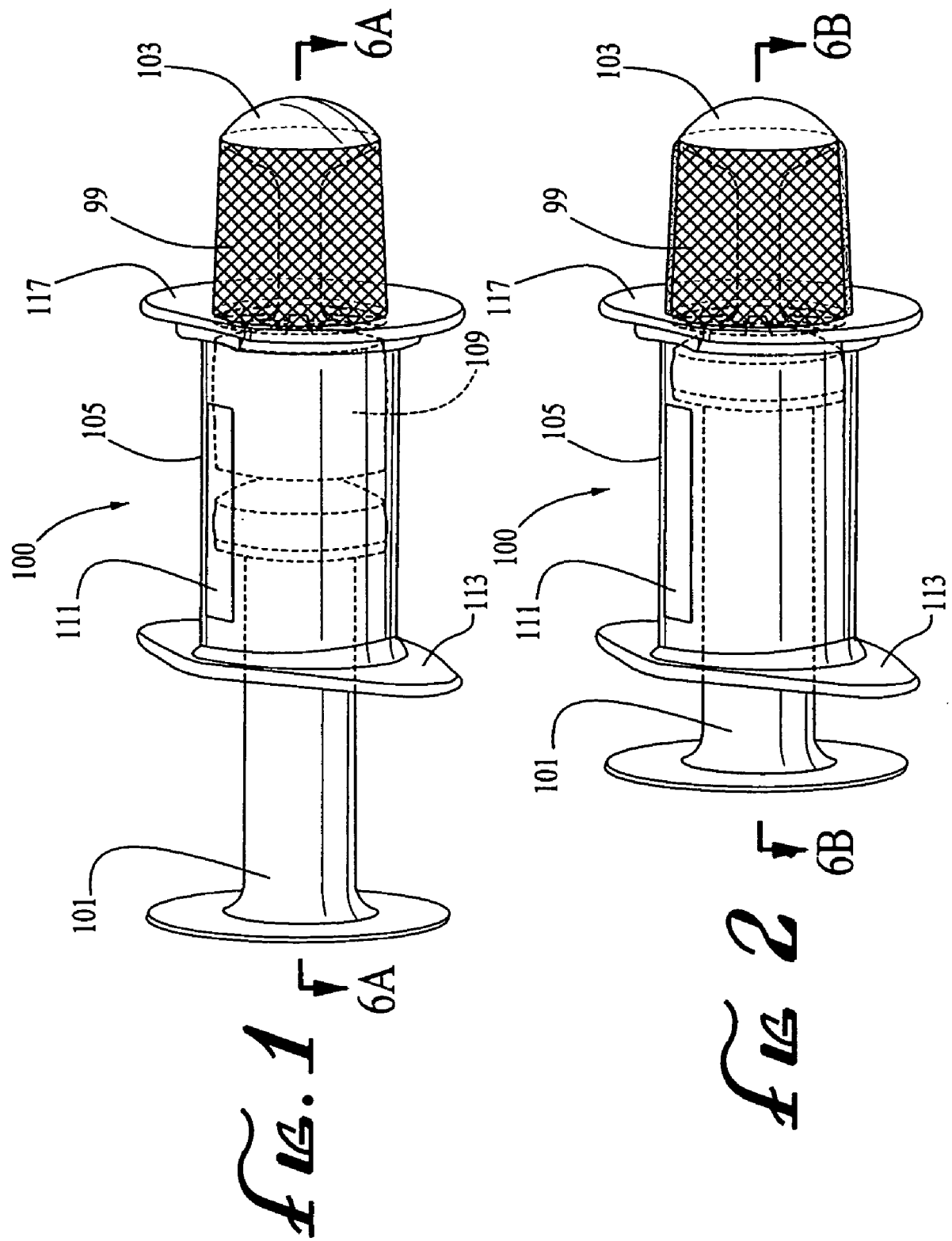

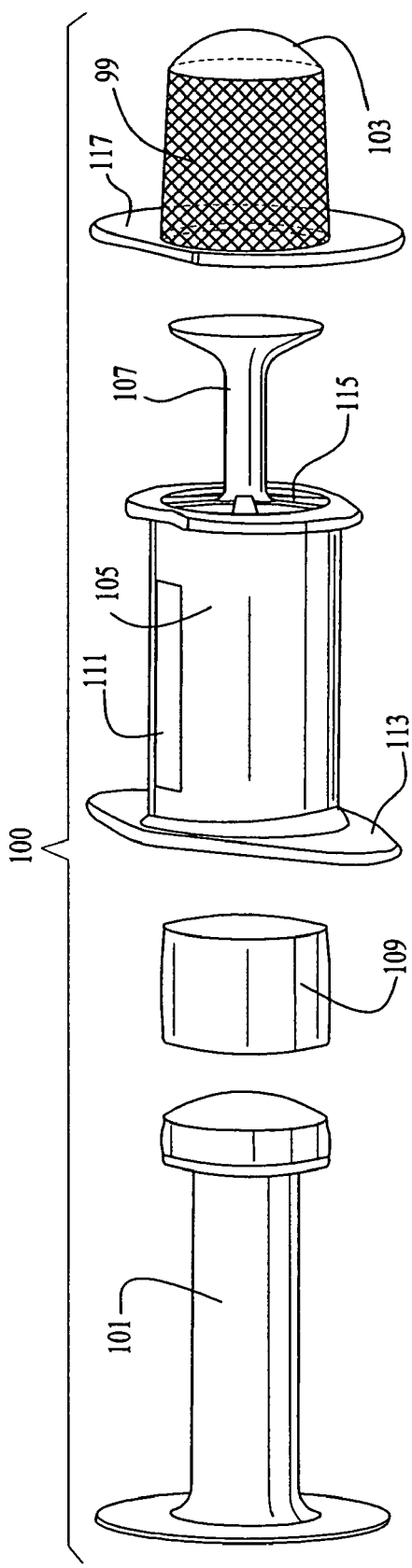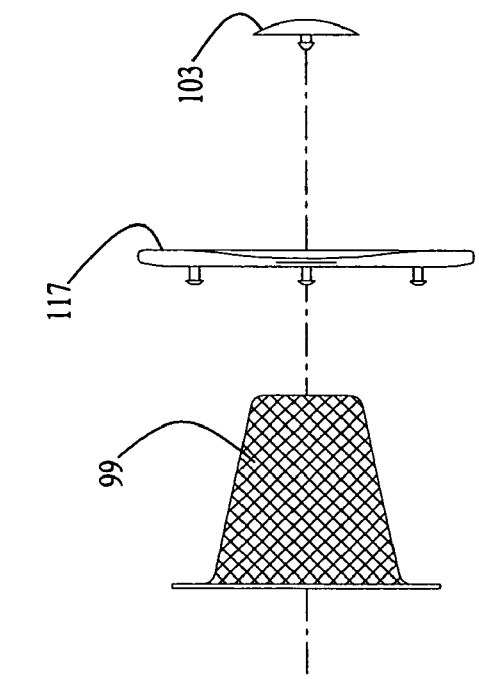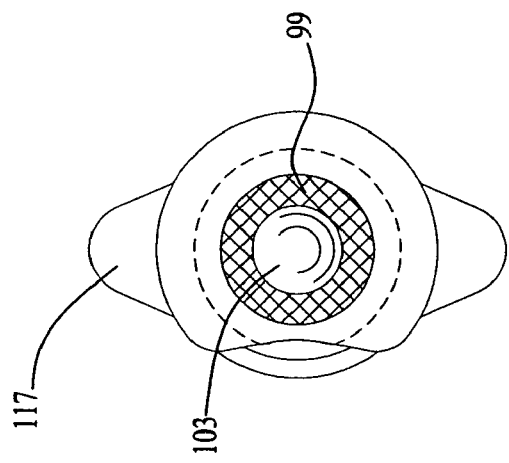

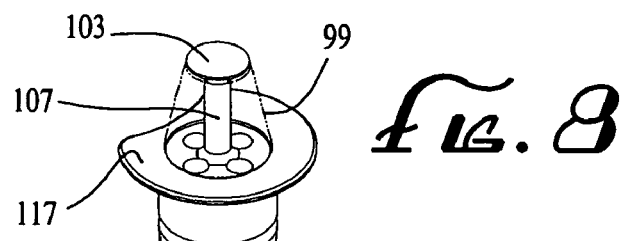
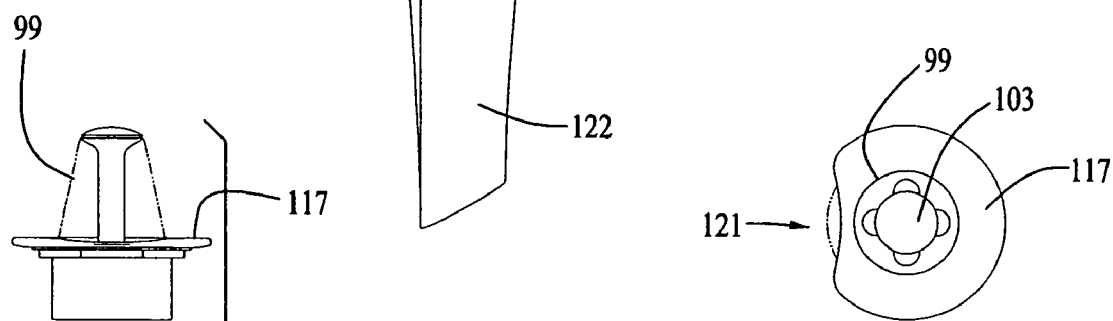
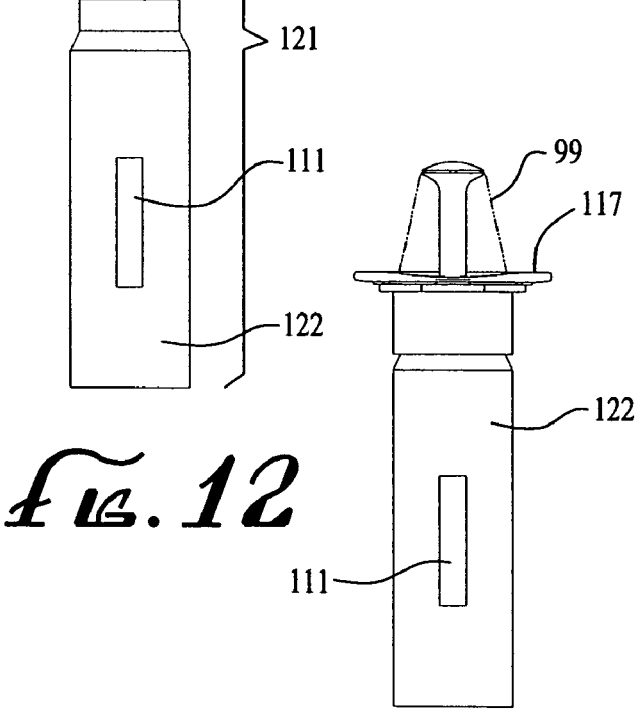
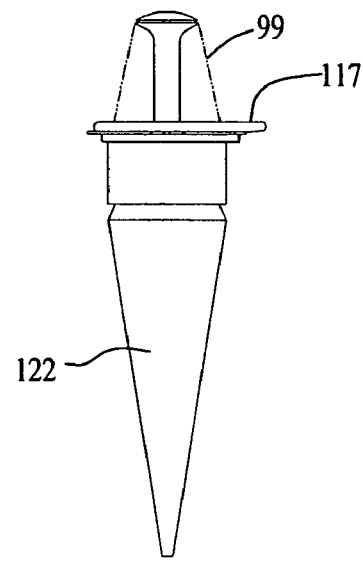

ENHANCED PRODUCTS AND PROCESSES FOR REMOVING CAVITY TISSUE

BACKGROUND OF THE DISCLOSURE

The present disclosure relates to depilatory systems, and to medical devices used for the removal of undesired epidermal tissue and related processes.

In particular, the present invention provides for a unique application for delicate body cavity treatment, for example for nasal hair removal, without injuring the texture of the delicate skin and which may be performed by a user, elegantly and simply without support from others necessarily required.

SUMMARY OF THE DISCLOSURE

Briefly stated, improved devices for removing dermis, for example, nasal hair using natural wax, or glue-based formulations. One embodiment uses telescoping tubes and there is wax or glue located in the inner tubes or between the tubes, whereby the tubes are located so that the inner one can extend or retract relative to the outer tube. Following heating the wax or glue for softening purposes, the same is applied to the inner part of, for example, the nasal cavity by emplacing the same in a desired naris and through application of force and wax extrusion through a cloth boot or otherwise, in combination with mild external pressure, removal is accomplished.

Those skilled in the arts of personal care, health, and beauty understand that a user's ears and various other cavity-based spaces can be cleansed and rendered more patent according to the teachings of the present disclosure as set forth herein and claimed below.

According to the instant disclosure there is provided a process for removing tissue from a mammal's body cavity, which comprises, in combination, heating a combined syringe-style and plunger-type of device having at least one of a bolus of wax and a plug of glue inside of it, inserting the device into the body cavity to be treated, urging the plunger mechanism from a first to a second position, extruding the wax or glue through a cloth boot which entraps detachable dermis lining the cavity and remains emplaced for a period of time, and removing the emplaced cloth and wax and entrapped dermal tissue.

According to the instant disclosure there is provided a novel device for removing undesired dermis from a body cavity of a mammal, which comprises, in combination: a syringe-style plunger mechanism operable to move from a first to a second position; a cavity for housing at least one of a bolus of wax and a glue plug; a guide mechanism to distribute the exudate to a desired location, and a cloth boot to trap hairs within a layer of at least one of glue and wax prior to removal.

Likewise, reasonable extensions of the teachings set forth herein are expressly contemplated to be within the scope of the instant disclosure, and such relief is hereby earnestly solicited.

BRIEF DESCRIPTION OF THE DRAWINGS

The instant disclosure is now described in greater detail with reference to an exemplary set of embodiments whereby like reference designating elements are denoted by similar reference designating numbers, and in which:

FIG. 1 shows a schematic view of an embodiment of the present disclosure in a first position;

FIG. 2 shows an embodiment of the present disclosure in a second position;

FIG. 3 shows an exploded view of an embodiment of the present disclosure;

FIG. 4 shows a partially exploded view of an embodiment of the disclosure, a distal, and of the present disclosure being detailed;

FIG. 5 shows a top view of an embodiment of the present disclosure;

DETAILED DESCRIPTION OF THE DISCLOSURE

Figure 6A:
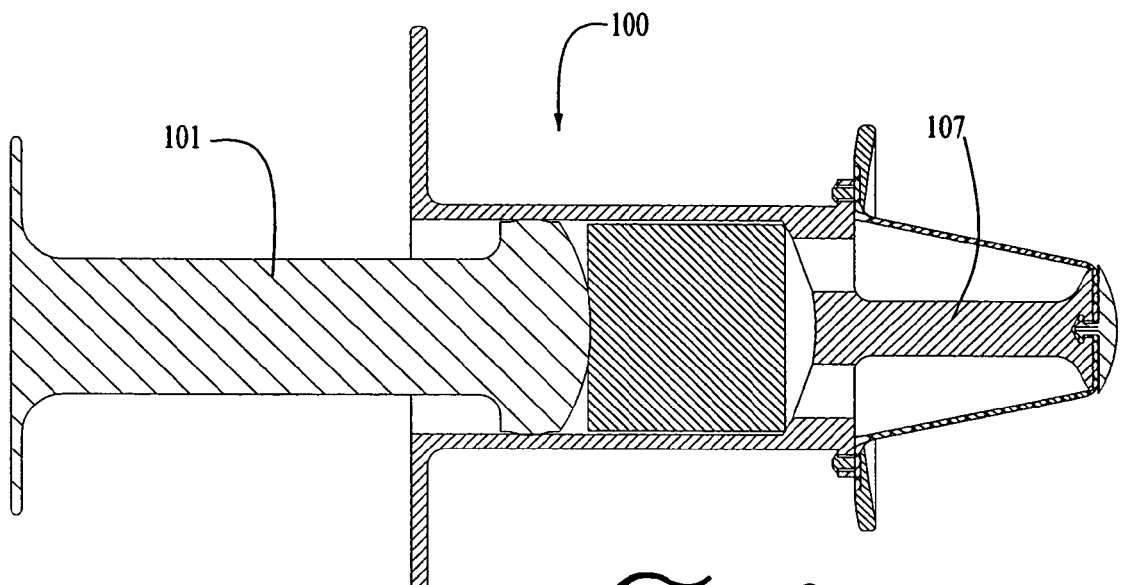
FIG. 6A shows an internal/partial cross-sectional view of an embodiment of the present disclosure.

The present inventor has discovered that novel enhanced personal hygiene mechanisms and regimens can be implemented through the use of a simple device and methods that allow a user to treat him or herself without the need for high cost, support and assistance from others, or the trapping either of a salon or medical suite.

In one aspect of the instant teachings, there is provided an appliance for wax depilation, especially for facial use, although the convenience and self-application enable a broad spectrum of alternate possible usages, which have been prototyped and undertaken by the present inventor.

For discussion purposes, and in exemplary fashion only, the use of the instant system for nose hair removal is offered for consideration. Those skilled in the art will understand that this illustrative set of teachings is merely that, and is not meant in any sense to be limiting of the teachings of the present invention.

It is known that various methods of wax depilation are in widespread use, especially for the removal of hairs from legs. Competition from lasers is limited by long-term damage data and chemical treatments likewise have serious downsides.

Known methods consist of melting the wax, in applying it to the leg in the molten state by means of a spatula, for example, in allowing the wax to solidify, then in exerting a pull on the wax in order to detach it from the skin. The hairs which are imprisoned in the wax are thus detached from the skin at the same time as the wax.

This method cannot readily be employed for depilating the face by the user's own unaided efforts. The internal and surfaces of the face are in fact very irregular and entail the need for a very high degree of accuracy of application of the wax in order to prevent any contact between the latter and very sensitive organs such as the mouth, the nostrils and the eyes.

One type of appliance which is already known serves to heat the wax or like material and to extrude this latter through an outlet nozzle. This apparatus consists of a kind of piston which is displaced by hand at one end of the appliance in order to discharge the wax in paste form within the appliance, however, it is cumbersome and requires noxious chemicals and the paste is an irritant as well.

Such an appliance cannot readily be applied to self-depilation of highly localized and sensitive areas of the skin and especially of the face, nor is it easily heated.

The aim of the present invention is to create an appliance for wax depilation which is particularly suitable for this purpose, namely elegant, simple, and safe self-depilation, or depilitation between partners, intimates or others in special relationships.

Thus, when the appliance is in service, the user pushes the carriage forward and causes a certain quantity of wax to be discharged from the nozzle by extrusion, which can be applied with accuracy.

The user may consequently carry out a very accurate depilation of the face without any attendant hazard to sensitive parts of the face.

By regulating the effort exerted the rate of extrusion of the wax from the outlet nozzle of the appliance can accordingly be controlled with accuracy.

Likewise, by providing a kit that can enable a user to undergo self-depilation, the present inventor has moved the world of consumer-driven personal health and beauty products forward.

EXAMPLE ONE

Nose Hair Removal

Understanding in general terms the process informs and enables use of the product. Referring now to FIG. 7, the device, as discussed above can be used for any number of applications, however one simple case is as a nose hair waxer 100 (as shown in FIGS. 1-6) is removed from its packaging 1, and may be heated, for example, by placing the same in a microwave oven 3. Any conventional oven as would be known to artisans, of the microwave type, will suffice for this purpose.

The present disclosure next employs a conventional strip of heat sensitive material, for example, using color-changing to indicate when it is ready to be removed 5. Those skilled in the art also understand that instructions and directions on timing for this are readily substitutable.

The next step 7, involves removal of nose waxer 100 from the microwave, followed by insertion of the same 100 into the selected nare, or nostril opening of a user 9.

Step 11 involves depressing plunger 101 all of the way until wax is extruded through cloth boot and user perceives the sensation of warmed wax, as proprioception inside of user's nare.

At this time, step 13 involves the application of a modicum of outside pressure to the external surface of user's nose. This is followed by an at least ten minute wax hardening step 15.

Finally, step 17 involves gentle removal of the nose waxer 100 from desired nare of user's nostril, removing those nose hairs that have become intermingled.

Turning now to FIG. 1, plunger handle aspect 101, is located at proximal of nose waxer 100. In operation, when heated wax bolus 109 (see FIG. 3) is forced out at distal end 103, through cloth boot 99, matingly engaging nose hairs of a user. FIG. 1 shows a first position, and likewise illustrates color indicating strip 111, as described above.

FIG. 2 shows a second position whereby plunger handle aspect 101 is urged from proximal to distal and 103 compressing wax bolus 109 to be extended through cloth boot 99. Those skilled in the art understand that any natural wax, for example beeswax, functions well as wax bolus or glue plug 109.

Referring now to FIG. 3, a disassembled view of device 100 shows plunger handle aspect 101, was bolus 109 and housing 105, wings 113 allow a user to grip device 100 and thrustingly insert plunger handle aspect 101 into aperture in housing 105 which is sized to engage the same.

Hammerhead 107 extends from housing 105, and includes grated section 115, having apertuces, slots, and the like means for permitting wax bolus to pass through, as melted. Distal end of hammerhead 107 engages end cap 103 about which cloth boot 99 is disposed. Nose guide 117 is adapted to fit into the nose of averaged user size noses, at the taper angle determined by the inventor to be optimal.

While the apparatus and method have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

Turning now to FIG. 4 and FIG. 5 top and side views are shown which further illustrate the relative spatial orientation and position of each of nose guide 117, end cap 103 and cloth boot 99.

Likewise, those skilled in the art will readily understand that alternate configuration remain within the skill level of those of ordinary skill in the trade, for example, alternate methods for exuding wax through the trunk of hammerhead 107 have been contemplated.

Figure 6B:
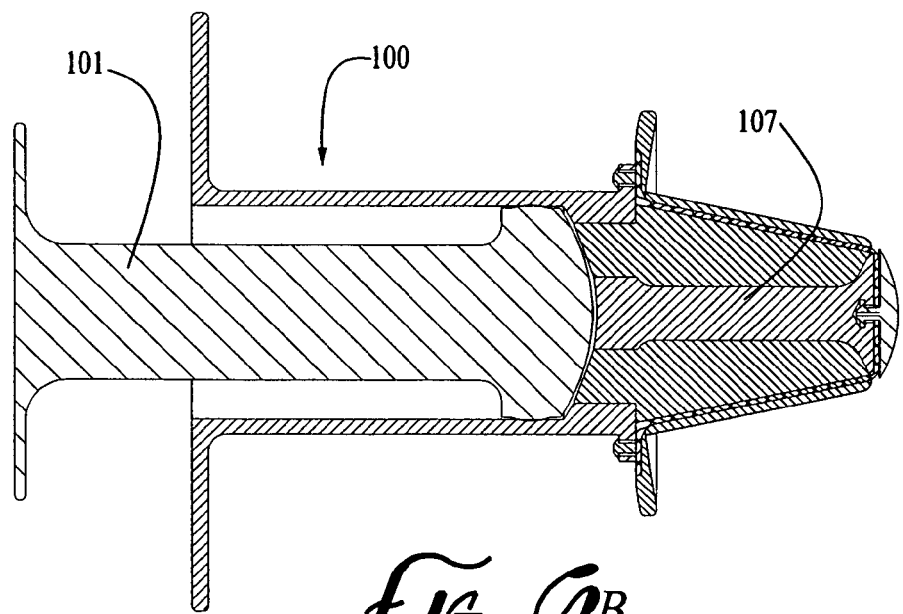
FIG. 6B shows an internal/partial cross-sectional view of an embodiment of the present disclosure.
Figure 7:
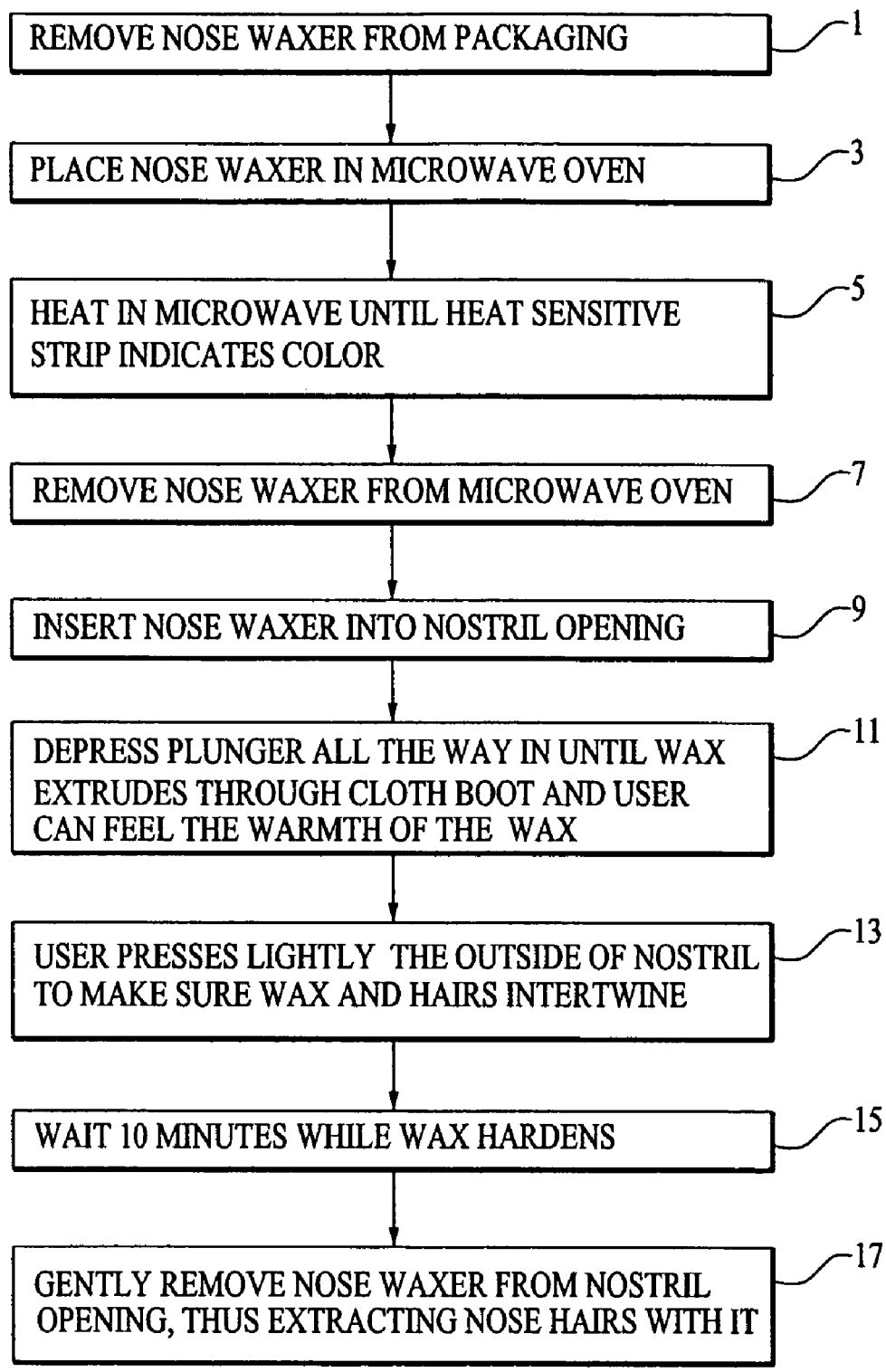
FIG. 7 illustrates a flow chart of a process according to the instant disclosure; and, FIGS. 8-12 illustrate an alternative embodiment according to the instant teachings.

Referring now to FIG. 6A and 6B a cross-sectional view depicts the activity of FIG. 2 shows a second position whereby plunger handle aspect 101 is urged from proximal to distal and 103 compressing wax bolus 109 to be extended through cloth boot 99. Those skilled in the art understand that any natural wax, for example beeswax, functions well as wax bolus or glue plug 109. Referring now to FIG. 3, a disassembled view of device 100 shows plunger handle aspect 101, was bolus 109 and housing 105, wings 113 allow a user to grip device 100 and thrustingly insert plunger handle aspect 101 into aperture in housing 105 which is sized to engage the same. Hammerhead 107 extends from housing 105, and includes grated section 115, having apertures, slots, and the like means for permitting wax bolus to pass through, as melted. Distal end of hammerhead 107 engages end cap 103 about which cloth boot 99 is disposed. Nose guide 117 is adapted to fit into the nose of averaged user size noses, at the taper angle determined by the inventor to be optimal.

FIG. 8-FIG. 12 depict and alternate embodiment of the instant disclosure and are functionally similar to the prior described devices and methods, however, artisans will realize that added convenience is achieved when a hand-squeezable assembly is substituted for the plunger mechanism.

FIG. 8 shows alternate assembly 122, used as discussed above for driving the wax/glue/desired formulations to distal end cap 103 by compressing for example (emplaced or ensconsed bolus 109 not shown) through alternate assembly 122 to be extended through cloth boot 99.

Referring now to FIG. 9, device 121 comes with the material to be melted already housed inside, according to disclosure of the present invention. This top view shows where the distal end of hammerhead 107 (not shown) engages end cap 103 about which cloth boot 99 is disposed. Nose guide 117 is adapted to fit into the nose of averaged user size noses, at the taper angle determined by the inventor to be optimal.

Once again it is noted that any natural wax, for example beeswax, functions well as wax bolus/glue plug/combination 109 (not shown), according to the teachings of the present disclosure. By applying pressure to alternate assembly 122, exudate is forced through, for example, the zone underneath cloth boot 99 (which may be any number of materials as known to artisans, so further discussion is omitted).

Referring now to FIG. 10, a disassembled view of alternate device 121 having incorporated bolus 109 (not shown) guides 117 allow a user to direct alternate assembly 122 into device 121 which is sized to engage the same. Hammerhead 107 (not completely shown) extends whereby distal end of hammerhead 107 engages end cap 103 about which cloth boot 99 is disposed. Nose guide 117 is adapted to fit into the nose of averaged user size noses, at the taper angle determined by the inventor to be optimal.

FIG. 11 shows a side view of alternate device 121 having incorporated bolus 109 (not shown) guides 117 allow a user to direct alternate assembly 122 into device 121 which is sized to engage the same. Hammerhead 107 (not completely shown) extends whereby distal end of hammerhead 107 engages end cap 103 about which cloth boot 99 is disposed. Cavity 117 is adapted to fit into a desired body cavity, at the taper angle determined by the inventor to be optimal.

While the apparatus, and processes have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. A process for removing tissue from a mammal's body cavity, which comprises, in combination:
    heating a combined syringe-style and plunger-type of device having at least one of a bolus of wax and a plug of glue inside of it;
    inserting the device into the body cavity defined by at least one of the naris of the nasal cavity and the external auditory cavity of the ear;
    urging a plunger mechanism from a first to a second position;
    extruding the wax or glue through a cloth boot which entraps detachable dermis lining the cavity and remains emplaced for a period of time; and
    removing the emplaced cloth and wax and entrapped dermal tissue.

2. The process of claim 1, wherein the heating is done with a microwave oven.

3. The process of claim 1, wherein the bolus of wax is a naturally occurring wax.

4. The process of claim 1, wherein the naturally occurring wax is at least one member of the group consisting of the yellow to grayish brown wax secreted by the honeybee for constructing honeycombs, commercial wax obtained by processing and purifying.

5. The process of claim 1 wherein the combined syringe-style and plunger-type of device is heated until a heat sensitive material indicates the wax or glue is ready by changing color.

6. A process for removing tissue from a mammal's body cavity, which comprises, in combination, the steps of:
    providing a one-hand actuable device having an upper piece for engaging a desired body cavity, and a detachable lower portion for housing at least one of a bolus of wax and a plug of glue inside of it;
    heating the device to achieve a phase change in the wax or glue from solid to liquidified as indicated by a color-changing heat sensitive material;
    inserting the device into the body cavity defined by at least one of the naris of the nasal cavity and the external auditory cavity of the ear;
    urging the molten wax or glue from a first to a second position;
    extruding the wax or glue through a cloth boot which entraps detachable dermis lining the cavity and remains emplaced for a period of time; and
    removing the emplaced cloth and wax and entrapped dermal tissue.

7. The process of claim 6, wherein the heating is done with a microwave oven.

8. The process of claim 6, wherein the bolus of wax is a naturally occurring wax.

* * * * *